United States Patent
Abdelgany et al.

(10) Patent No.: US 7,819,902 B2
(45) Date of Patent: Oct. 26, 2010

(54) MEDIALISED ROD PEDICLE SCREW ASSEMBLY

(75) Inventors: Mahmoud F. Abdelgany, Rockaway, NJ (US); Young Hoon Oh, Wayne, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 1669 days.

(21) Appl. No.: 11/048,189

(22) Filed: Feb. 1, 2005

(65) Prior Publication Data
US 2005/0192572 A1 Sep. 1, 2005

Related U.S. Application Data

(60) Provisional application No. 60/548,543, filed on Feb. 27, 2004, provisional application No. 60/622,646, filed on Oct. 27, 2004.

(51) Int. Cl.
A61B 17/70 (2006.01)
(52) U.S. Cl. ........................ 606/267; 606/279
(58) Field of Classification Search .................. 606/60, 606/246, 250–253, 264–275, 278, 279
See application file for complete search history.

(56) References Cited

U.S. PATENT DOCUMENTS

| | | | |
|---|---|---|---|
| 3,054,321 A | 9/1962 | Macchia | |
| 4,887,596 A | 12/1989 | Sherman | |
| 4,946,458 A | 8/1990 | Harms et al. | |
| 5,067,955 A | 11/1991 | Cotrel | |
| 5,129,388 A | 7/1992 | Vignaud et al. | |
| 5,246,442 A | 9/1993 | Ashman et al. | |
| 5,360,431 A | 11/1994 | Puno et al. | |
| 5,443,467 A | 8/1995 | Biedermann et al. | |
| 5,466,237 A | 11/1995 | Byrd, III et al. | |
| 5,474,555 A | 12/1995 | Puno et al. | |
| 5,476,464 A | 12/1995 | Metz-Stavenhagen et al. | |
| 5,520,689 A | 5/1996 | Schlapfer et al. | |
| 5,536,268 A | 7/1996 | Griss | |
| 5,545,165 A | 8/1996 | Biedermann et al. | |
| 5,669,911 A | 9/1997 | Errico et al. | |
| 5,672,176 A | 9/1997 | Biedermann et al. | |
| 5,733,286 A | 3/1998 | Errico et al. | |
| 5,752,957 A | 5/1998 | Ralph et al. | |
| 5,863,293 A | 1/1999 | Richelsoph | |
| 5,879,350 A | 3/1999 | Sherman et al. | |
| 5,882,350 A | 3/1999 | Ralph et al. | |

(Continued)

FOREIGN PATENT DOCUMENTS

DE 19950075 4/2001

(Continued)

*Primary Examiner*—Thomas C Barrett
*Assistant Examiner*—Michael J Araj
(74) *Attorney, Agent, or Firm*—Rahman LLC

(57) ABSTRACT

A pedicle screw assembly and method of assembly comprises a longitudinal member; a bendable ball ring adapted to receive the longitudinal member; a poly stem comprising a bendable male bulbous end; and a connector comprising a pair of first apertures adapted to receive the poly stem; and a second aperture adapted to receive the ball ring and the longitudinal member, wherein the second aperture is transverse to the first aperture. The assembly further comprises a bone fixator component comprising a female socket adapted to receive the poly stem; and a blocker pin adapted to engage the poly stem and to secure the longitudinal member.

19 Claims, 16 Drawing Sheets

U.S. PATENT DOCUMENTS

| | | | |
|---|---|---|---|
| 5,885,286 A | 3/1999 | Sherman et al. | |
| 5,951,553 A | 9/1999 | Betz et al. | |
| 5,964,760 A | 10/1999 | Richelsoph | |
| 5,964,767 A | 10/1999 | Tapia et al. | |
| 5,989,250 A | 11/1999 | Wagner et al. | |
| 6,022,350 A | 2/2000 | Ganem | |
| 6,030,389 A | 2/2000 | Wagner et al. | |
| 6,045,579 A | 4/2000 | Hochshuler et al. | |
| 6,050,997 A * | 4/2000 | Mullane | 606/250 |
| 6,053,917 A | 4/2000 | Sherman et al. | |
| 6,063,090 A | 5/2000 | Schlapfer | |
| 6,074,391 A | 6/2000 | Metz-Stavenhagen et al. | |
| 6,077,262 A | 6/2000 | Schlapfer et al. | |
| 6,090,110 A | 7/2000 | Metz-Stavenhagen | |
| 6,090,111 A | 7/2000 | Nichols | |
| 6,113,601 A | 9/2000 | Tatar | |
| 6,132,430 A | 10/2000 | Wagner | |
| 6,132,432 A | 10/2000 | Richelsoph | |
| 6,187,005 B1 | 2/2001 | Brace et al. | |
| 6,248,105 B1 | 6/2001 | Schlapfer et al. | |
| 6,273,888 B1 | 8/2001 | Justis | |
| 6,280,442 B1 | 8/2001 | Barker et al. | |
| 6,290,703 B1 | 9/2001 | Ganem | |
| 6,302,888 B1 | 10/2001 | Mellinger et al. | |
| RE37,665 E | 4/2002 | Ralph et al. | |
| 6,368,321 B1 | 4/2002 | Jackson | |
| 6,371,957 B1 | 4/2002 | Amrein et al. | |
| 6,416,515 B1 | 7/2002 | Wagner | |
| 6,454,769 B2 | 9/2002 | Wagner et al. | |
| 6,475,218 B2 | 11/2002 | Gournay et al. | |
| 6,485,491 B1 | 11/2002 | Farris et al. | |
| 6,485,492 B1 | 11/2002 | Halm et al. | |
| 6,488,681 B2 | 12/2002 | Martin et al. | |
| 6,554,834 B1 | 4/2003 | Crozet et al. | |
| 6,562,040 B1 | 5/2003 | Wagner | |
| 6,565,565 B1 | 5/2003 | Yuan et al. | |
| 6,595,992 B1 | 7/2003 | Wagner et al. | |
| 6,610,063 B2 | 8/2003 | Kumar et al. | |
| 6,613,050 B1 | 9/2003 | Wagner et al. | |
| 6,623,485 B2 | 9/2003 | Doubler et al. | |
| 6,641,586 B2 | 11/2003 | Varieur | |
| 6,648,888 B1 | 11/2003 | Shluzas | |
| 6,660,004 B2 | 12/2003 | Barker et al. | |
| 6,736,820 B2 | 5/2004 | Biedermann et al. | |
| 6,780,186 B2 | 8/2004 | Errico et al. | |
| 6,858,030 B2 | 2/2005 | Martin et al. | |
| 6,974,460 B2 | 12/2005 | Carbone et al. | |
| 7,022,122 B2 | 4/2006 | Amrein et al. | |
| RE39,089 E | 5/2006 | Ralph et al. | |
| 7,118,571 B2 | 10/2006 | Kumar et al. | |
| 7,128,743 B2 | 10/2006 | Metz-Stavenhagen | |
| 7,186,255 B2 * | 3/2007 | Baynham et al. | 606/266 |
| 2002/0010467 A1 * | 1/2002 | Cooper et al. | 606/61 |
| 2003/0055426 A1 | 3/2003 | Carbone et al. | |
| 2003/0073996 A1 | 4/2003 | Doubler et al. | |
| 2004/0153077 A1 | 8/2004 | Biedermann et al. | |
| 2004/0215190 A1 * | 10/2004 | Nguyen et al. | 606/61 |
| 2006/0052783 A1 * | 3/2006 | Dant et al. | 606/61 |

FOREIGN PATENT DOCUMENTS

| | | |
|---|---|---|
| EP | 1090595 A2 | 4/2001 |
| EP | 1254640 A2 | 11/2002 |
| EP | 1293168 A2 | 3/2003 |
| WO | WO9834554 | 8/1998 |
| WO | WO9955246 A1 | 11/1999 |
| WO | WO0122893 A1 | 4/2001 |
| WO | WO03068088 A1 | 8/2003 |

* cited by examiner

FIG. 2D  Section B-B

FIG. 2C  Section A-A

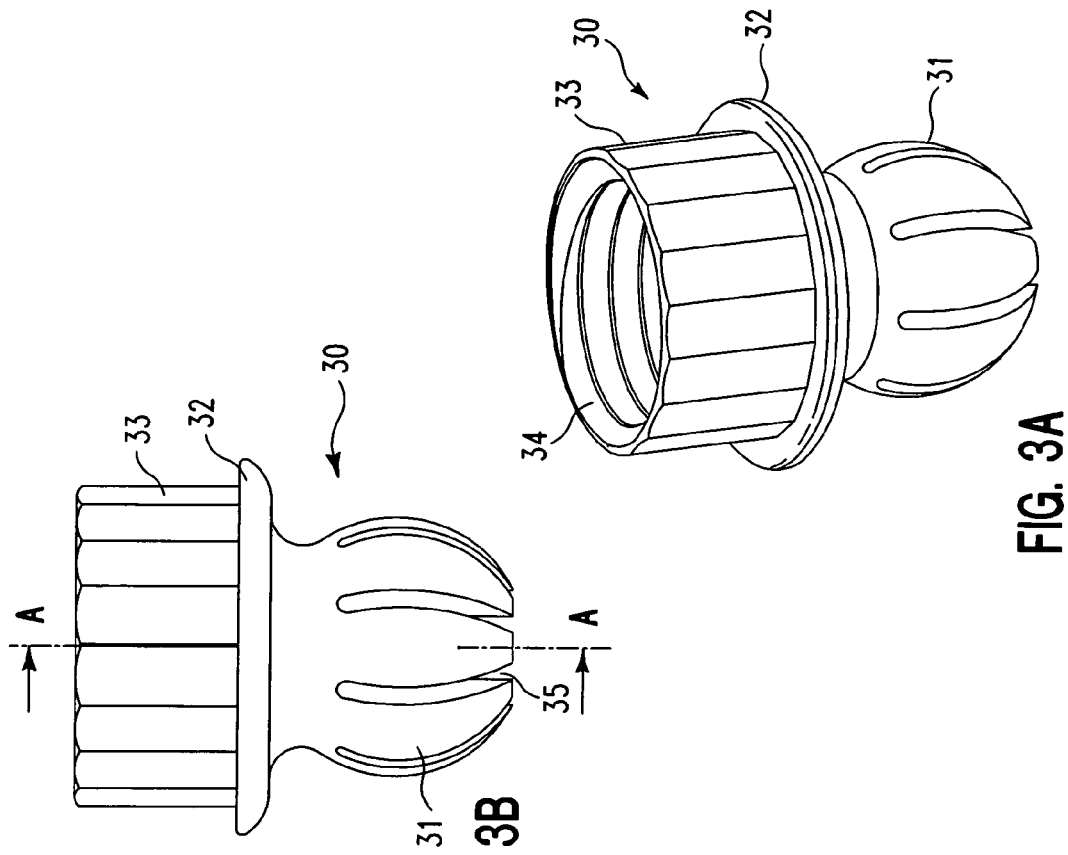
FIG. 3A
FIG. 3B
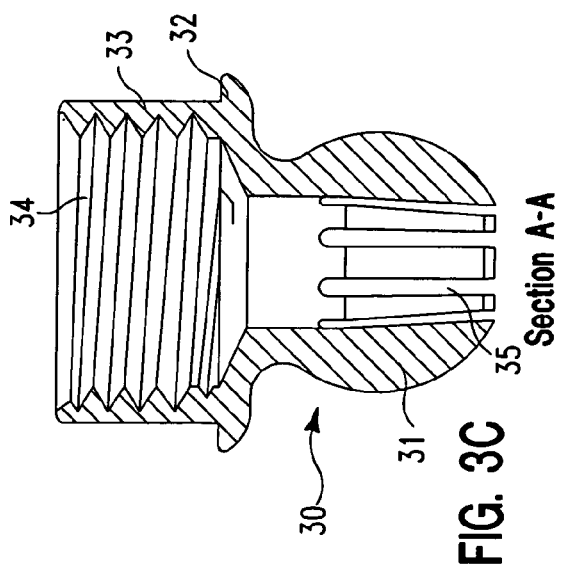
FIG. 3C
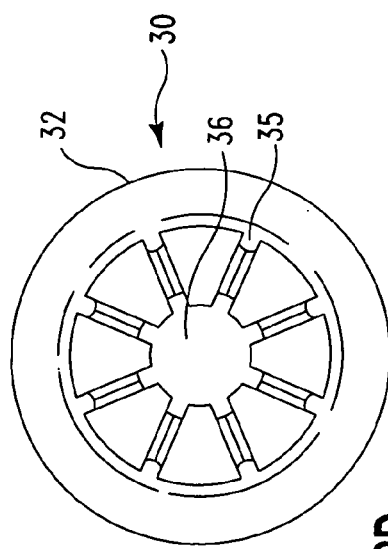
FIG. 3D

Section A-A

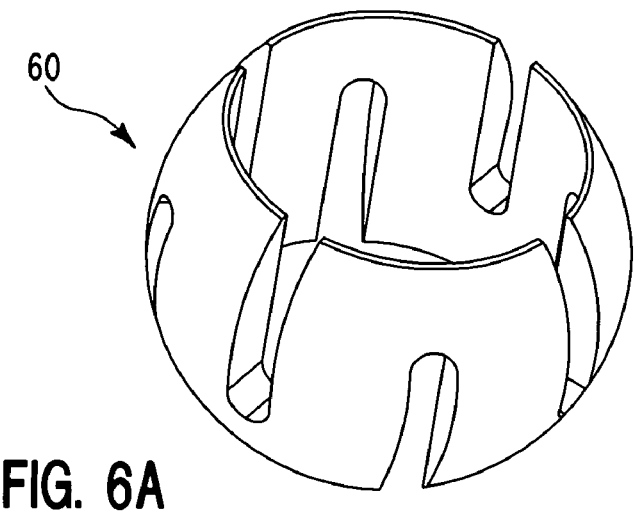
FIG. 6A
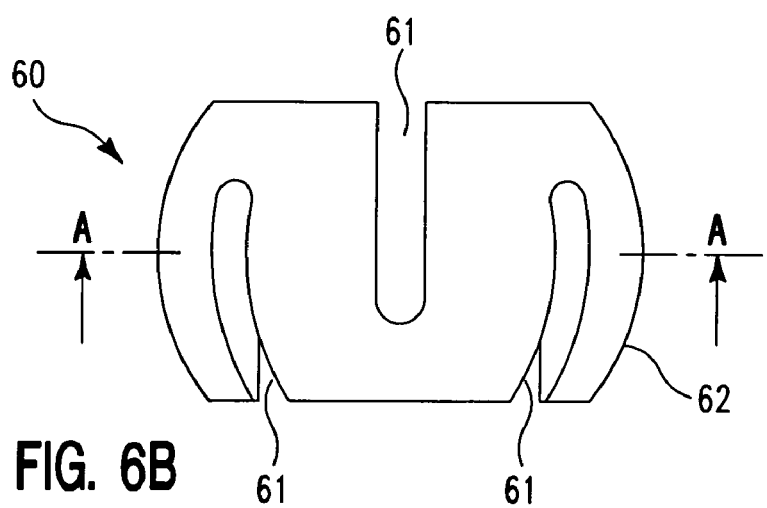
FIG. 6B
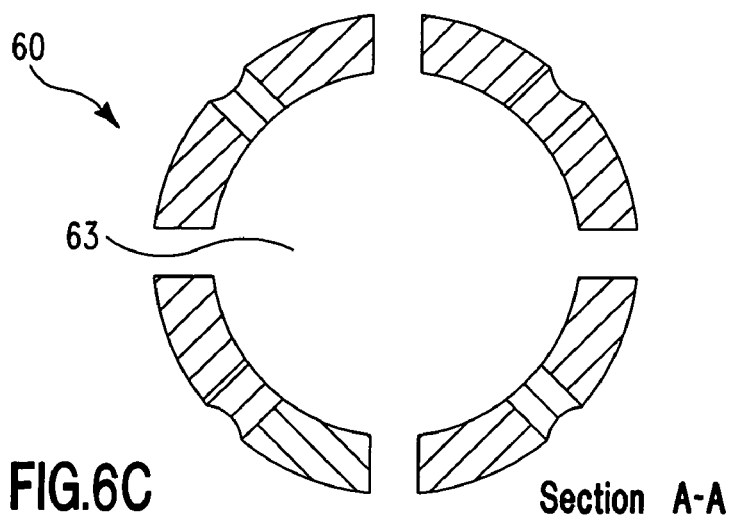
FIG. 6C     Section A-A

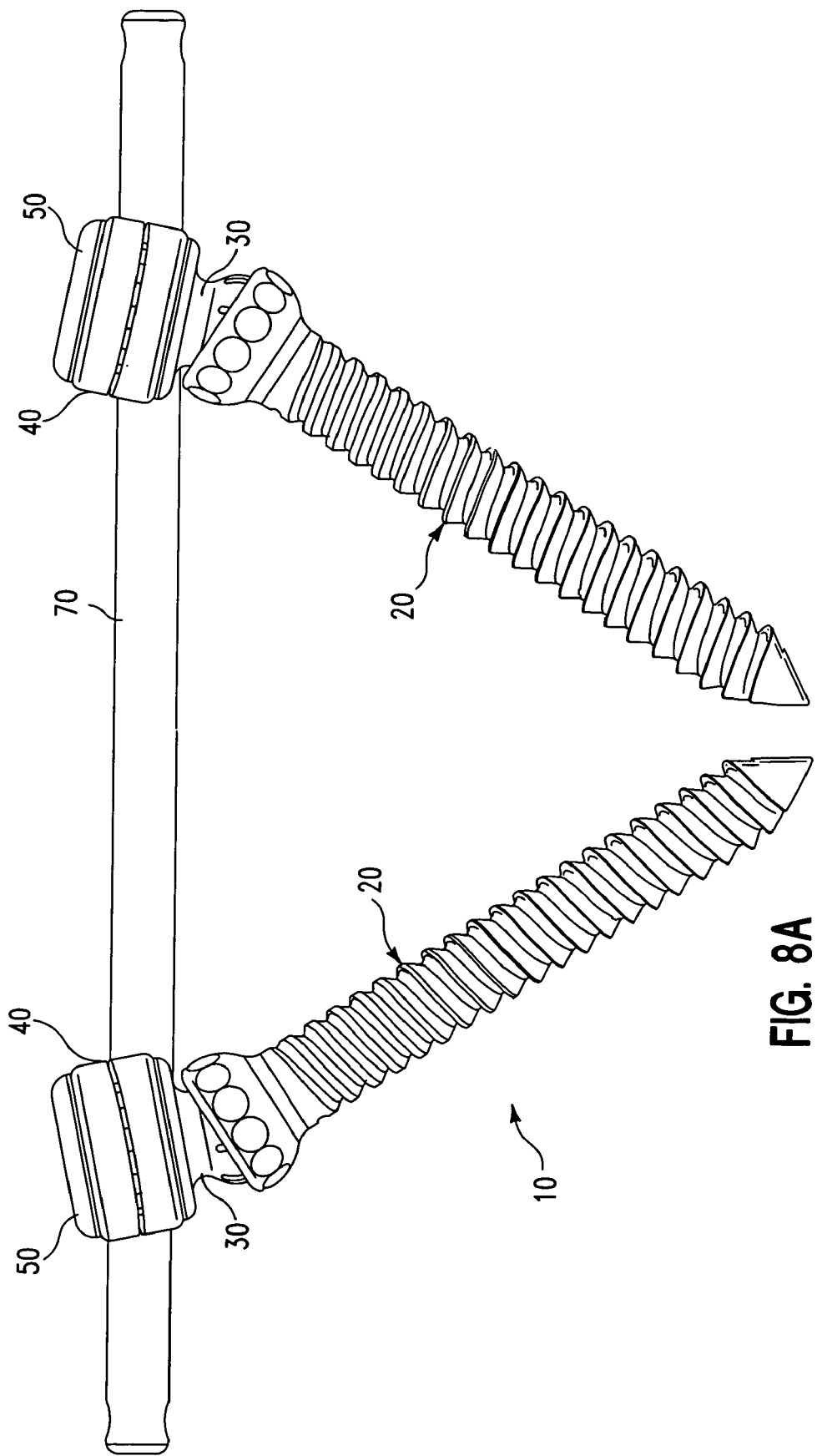

MEDIALISED ROD PEDICLE SCREW ASSEMBLY

CROSS REFERENCE TO RELATED APPLICATION

This application claims the benefit of U.S. Provisional Patent Application No. 60/548,543 filed on Feb. 27, 2004 and U.S. Provisional Patent Application No. 60/622,646 filed on Oct. 27, 2004, the contents of which in their entireties are herein incorporated by reference.

BACKGROUND OF THE INVENTION

1. Field of the Invention

The embodiments of the invention generally relate to medical devices and assemblies, and more particularly to an orthopedic surgical implant assembly used in the field of surgical lumbar, thoracic and cervical spine treatment.

2. Description of the Related Art

Surgical procedures treating spinal injuries are one of the most complex and challenging surgeries for both the patient and the surgeon. When there are various deformities, trauma, or fractures of the vertebra, surgeons may attempt to "fuse" them together by attaching screw-like devices into the pedicles of the spine and thereby connecting several vertebrae (typically two or more) using a semi-rigid rod. However, due to the complexity of the human anatomy, most surgeons must bend the rod (causing notches thereby reducing fatigue resistance) before placing them into two or more non-aligned pedicle screws in order to properly stabilize the pedicle screw assembly within the patient's body. However, this bending causes notches and reduces fatigue resistance and wastes valuable surgery time before the surgeon is able to insert the rod. That is, the surgeon must sacrifice the freedom of optimal screw placement in the spine for ease of construct assembly.

Depending on the purpose of the spine surgery, indications, and patient size, surgeons must pre-operatively choose between different spinal systems with differing rod sizes pre-operatively sometimes causing delays in surgery while waiting for more adequate systems to be sterilized. Some surgeons prefer monoaxial screws for rigidity, while some sacrifice rigidity for surgical flexibility in screw placement. Therefore, a system is needed to accommodate both theories. For example, during scoliosis surgery conventional polyaxial systems typically cannot lock into a desired position to persuade the spinal column into the desired correction before final construct assembly.

Most conventional top loading polyaxial spine screws do not do enough to address cantilever failure of the assembly components. Additionally, most conventional polyaxial screws generally do not offer enough flexibility because the rod sits too closely on top of the center of rotation of the bone screw producing a smaller arc of rotation. Moreover, most conventional polyaxial screw assemblies do not offer enough freedom and have too much of a "fiddle factor" in fabrication. Additionally, most conventional pedicle screw assemblies depend on deforming and notching the rod to lock it axially and rotationally to the screw head thereby reducing the life of the rod by increasing the mechanical fatigue of the rod. Thus, there remains a need for a new and improved pedicle screw assembly capable of overcoming the limitations of the conventional designs thereby providing the surgeon with improved intra-operative flexibility and the patient with an improved prognosis for better and complete rehabilitation.

SUMMARY OF THE INVENTION

In view of the foregoing, an embodiment of the invention provides an assembly comprising a ball ring; a stem component comprising a bulbous end; a fixator component adapted to receive the bulbous end of the stem component; and a connector comprising a first aperture; and a second aperture. The assembly further comprises a blocker pin adapted to engage the stem component. Preferably, the fixator component comprises a threaded end; and a pocket end opposite the threaded end, wherein the pocket end preferably comprises a concave inner portion and a dimpled outer portion.

The stem component preferably further comprises a threaded open end opposite the bulbous end, wherein the bulbous end comprises a plurality of slots; and a hole in the bulbous end terminating at the plurality of slots, wherein the hole is adapted to receive the blocker pin. The ball ring preferably comprises a curved body having a plurality of trans-radial cuts; and a hole configured in the curved body and adapted to receive a longitudinal member. The first aperture is adapted to receive the stem component. The second aperture is adapted to accommodate the ball ring and to receive a longitudinal member, wherein the second aperture is transverse to the first aperture.

The connector preferably comprises a medial portion comprising the second aperture; and a pair of prongs connected by the medial portion, wherein the pair of prongs comprise the first aperture, wherein the connector may comprise a gap separating the pair of prongs from one another. The blocker pin comprises a lower section adapted to fit into the hole in the bulbous end of the stem component; a threaded portion adjacent to the lower section and adapted to mate with the threaded open end of the stem component; and an upper section adjacent to the threaded portion, wherein the upper section is adapted to engage one of the pair of prongs of the stem component. Preferably, each of the bulbous end and the ball ring are bendable.

Another aspect of the invention provides a pedicle screw assembly comprising a longitudinal member; a bendable ball ring adapted to receive the longitudinal member; a poly stem ring comprising a bendable male bulbous end; and a connector comprising a pair of first apertures adapted to receive the poly stem; and a second aperture adapted to receive the ball ring and the longitudinal member, wherein the second aperture is transverse to the first aperture.

The assembly further comprises a bone fixator component comprising a female socket adapted to receive the poly stem; and a blocker pin adapted to engage the poly stem and to secure the longitudinal member. Preferably, the poly stem further comprises a threaded open end opposite the bulbous end, wherein the bulbous end comprises a plurality of slots; a hole in the bulbous end terminating at the plurality of slots, wherein the hole is adapted to receive the blocker pin. The pair of first apertures is preferably adapted to receive the poly stem.

Preferably, the connector comprises a medial portion comprising the second aperture; and a pair of prongs connected by the medial portion, wherein the pair of prongs comprise the pair of first apertures, and wherein the connector may comprise a gap separating the pair of prongs from one another. Preferably, the blocker pin comprises a lower section adapted to fit into the hole in the bulbous end of the poly stem; a threaded portion adjacent to the lower section and adapted to mate with the threaded open end of the poly stem; and an upper section adjacent to the threaded portion, wherein the upper section is adapted to engage one of the pair of prongs of the poly stem.

Another embodiment of the invention provides a method of assembling a pedicle screw assembly, wherein the method comprises attaching a stem component comprising a male bulbous end to a bone fixator component comprising a female socket; securing the bone fixator component in a bone; engaging a connector over the stem component, wherein the connector comprises a first aperture for receiving the stem component and a second aperture transverse to the first aperture; inserting a ball ring into the second aperture of the connector; inserting a longitudinal member in the ball ring; inserting a blocker pin in the first aperture of the connector; and engaging the blocker pin with the stem component. Moreover, the engagement of the blocker pin with the stem component causes expansion of the male bulbous end of the stem component in the female socket of the bone fixator component. Additionally, the engagement of the blocker pin with the stem component causes tightening of the ball ring thereby causing the ball ring to secure the longitudinal member.

The embodiments of the invention provide a polyaxial spinal screw assembly that provides greater freedom in screw placement while maintaining an adequate profile in the spinal anatomy. The added freedom is accomplished by having three separate features that offer various degrees of flexibility. The embodiments of the invention also provide greater freedom by allowing the surgeon to place the connector right side up or upside down to accommodate various heights on the longitudinal member without leaving the anchor part outside the anchor anatomy. The embodiments of the invention also provide a lower profile by allowing the polyaxial center of rotation to be buried within the pedicle or anatomy thereby gaining valuable space to fasten the longitudinal member or plate. In an alternative embodiment, a ceramic coated ball joint is used for improved wear resistance that would not be rigid, but rather, would offer a predetermined resistance force to function as a dynamic rod system to provide load sharing with the natural human disc or an artificial disk.

Generally, the embodiments of the invention provide an improvement in the field of surgical lumbar and thoracic and cervical spine treatment; it may be used anteriorly or posteriorly. The embodiments of the invention can be utilized in surgeries to achieve anterior lumbar interbody fusion, posterior lumbar interbody fusion, transverse lumbar interbody fusion, degenerative disc disease, adult and pediatric scoliosis as a fixation device, and posterior cervical fusion.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which:

FIG. 2(C) illustrates a cross-sectional side view cut along section A-A of the bone fixator component of FIG. 2(B) according to an embodiment of the invention;

FIG. 2(D) illustrates a cross-sectional top view cut along section B-B of the bone fixator component of FIG. 2(B) according to an embodiment of the invention;

FIG. 3(A) illustrates a perspective view of the poly stem of FIG. 1 according to an embodiment of the invention;

FIG. 3(B) illustrates a front view of the poly stem of FIG. 3(A) according to an embodiment of the invention;

FIG. 3(C) illustrates a cross-sectional side view cut along section A-A of the poly stem of FIG. 3(B) according to an embodiment of the invention;

FIG. 3(D) illustrates a bottom view of the poly stem of FIG. 3(B) according to an embodiment of the invention;

FIG. 6(A) illustrates a perspective view of the ball ring of FIG. 1 according to an embodiment of the invention;

FIG. 6(B) illustrates a side view of the ball ring of FIG. 6(A) according to an embodiment of the invention;

FIG. 6(C) illustrates a cross-sectional top view cut along section A-A of the ball ring of FIG. 6(B) according to an embodiment of the invention;

FIG. 8(A) illustrates a front view of a fully engaged screw assembly in various stages of angulation with an upright connector configuration according to an embodiment of the invention;

DETAILED DESCRIPTION OF PREFERRED EMBODIMENTS OF THE INVENTION

Figure 1:
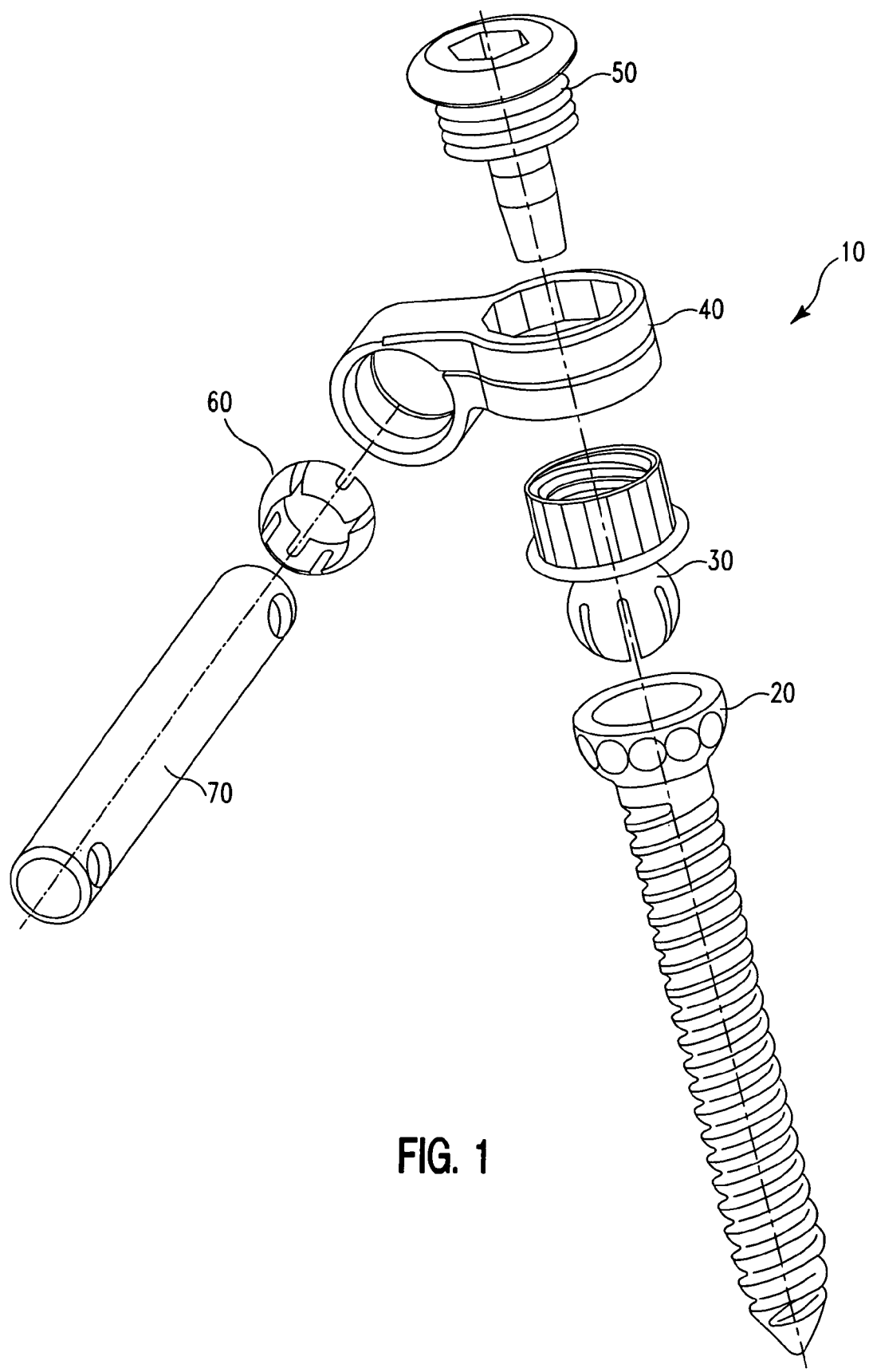
FIG. 1 illustrates an exploded view of the screw assembly according to an embodiment of the invention.
Figure 2A:
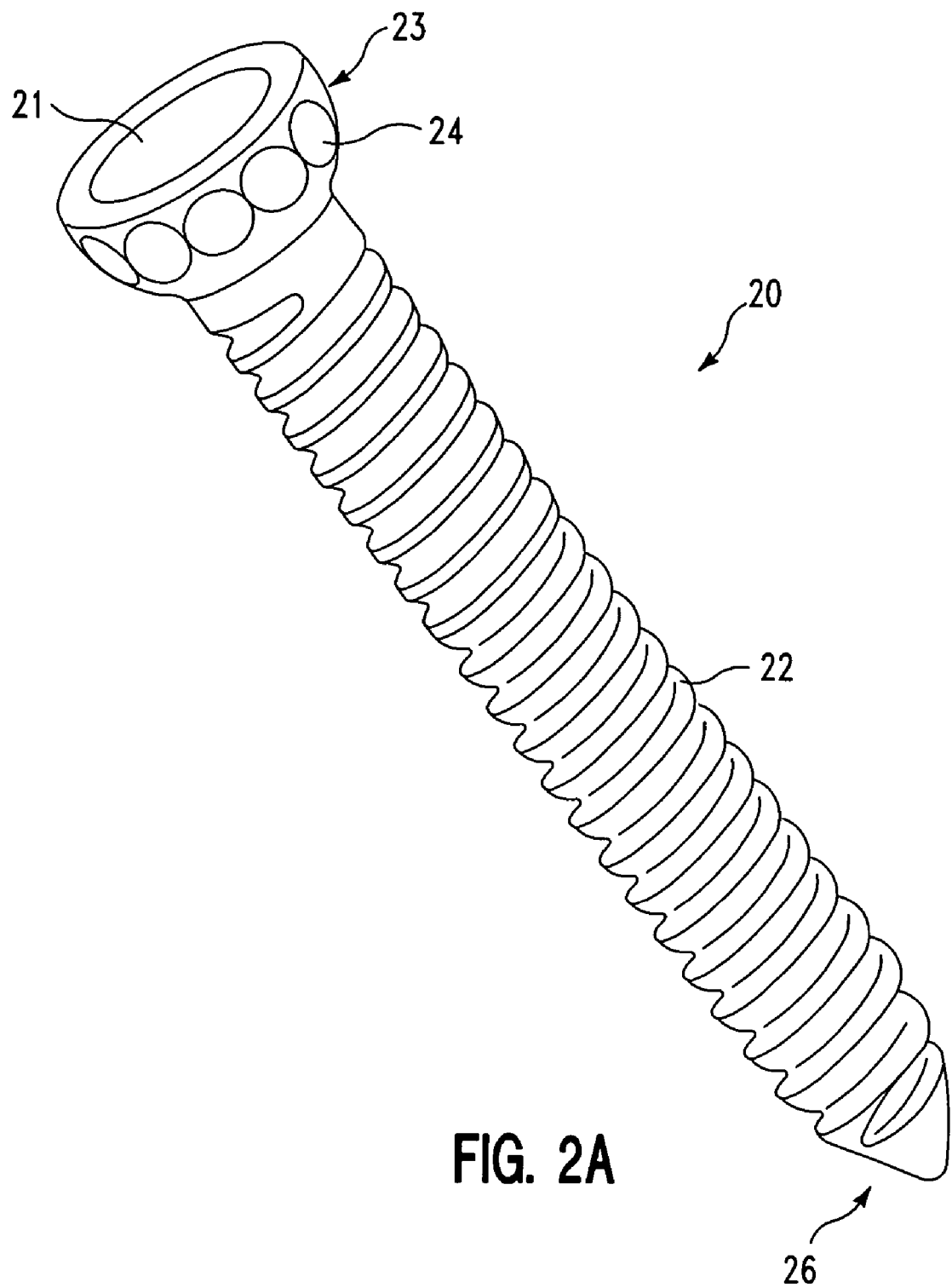
FIG. 2(A) illustrates a perspective view of the bone fixator component of FIG. 1 according to an embodiment of the invention.
Figure 2B:
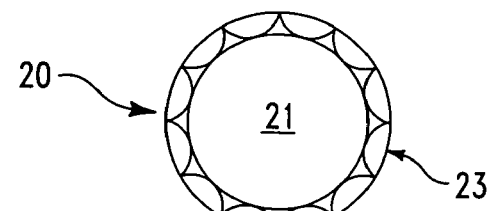
FIG. 2(B) illustrates a front view of the bone fixator component of FIG. 2(A) according to an embodiment of the invention.
Figure 2B:
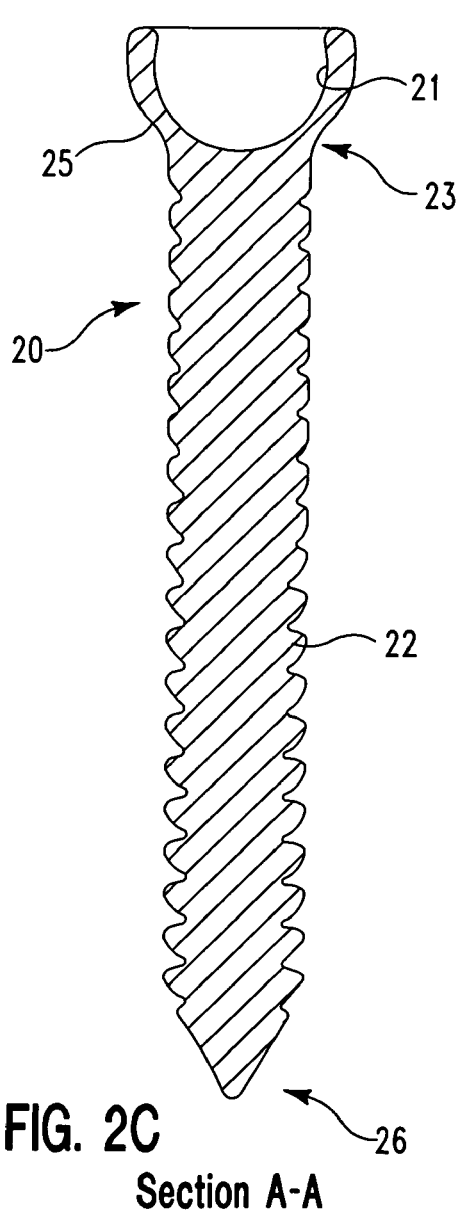
Figure 2B:
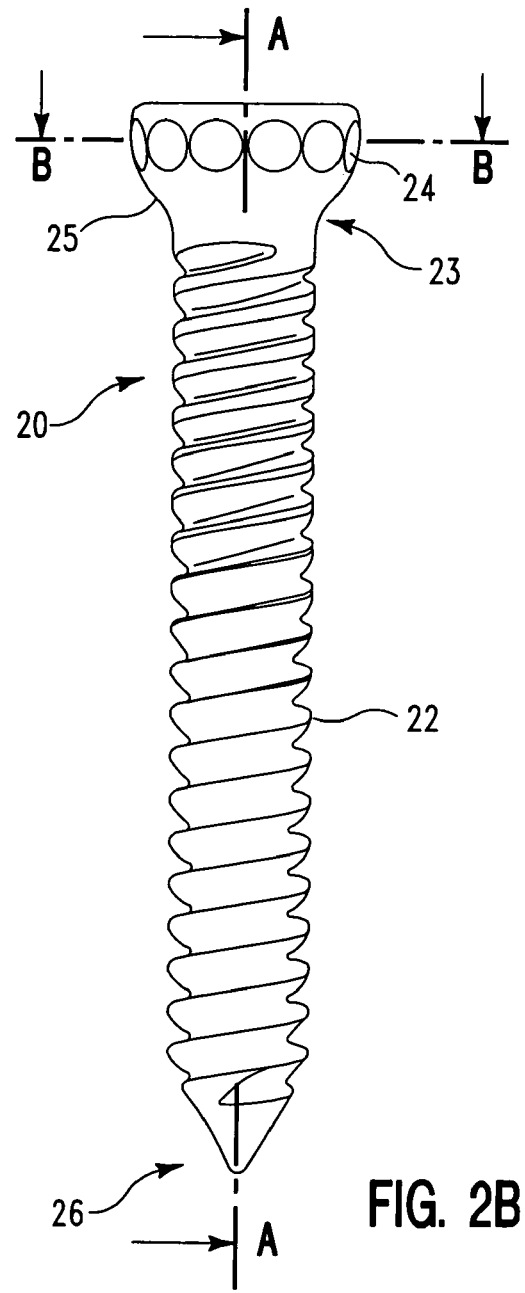
Figure 4D:
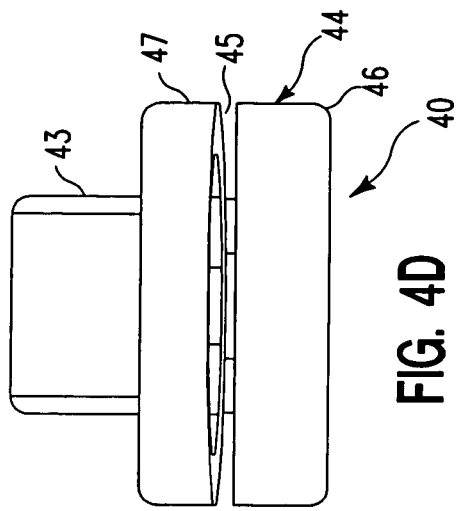
FIG. 4(D) illustrates a side view of the connector of FIG. 4(B) according to an embodiment of the invention.
Figure 4A:
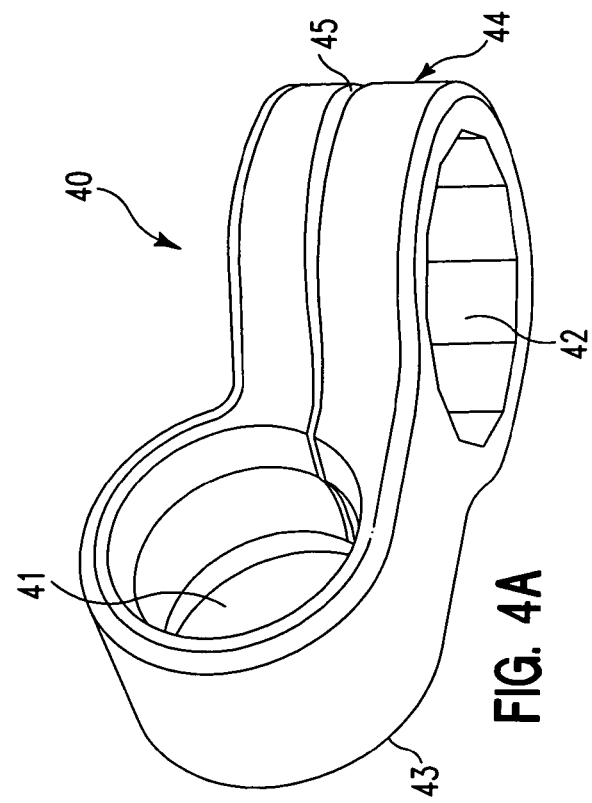
FIG. 4(A) illustrates a perspective view of the connector of FIG. 1 according to an embodiment of the invention.
Figure 4C:
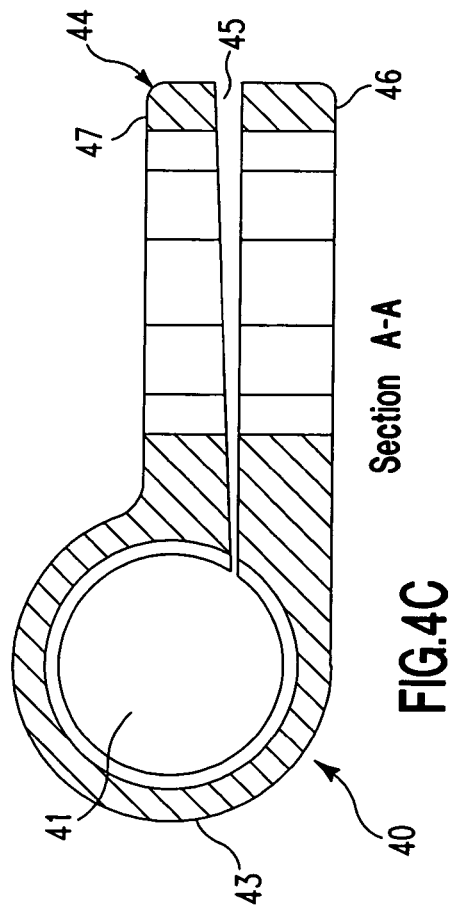
FIG. 4(C) illustrates a cross-sectional front view cut along section A-A of the connector of FIG. 4(B) according to an embodiment of the invention.
Figure 4B:
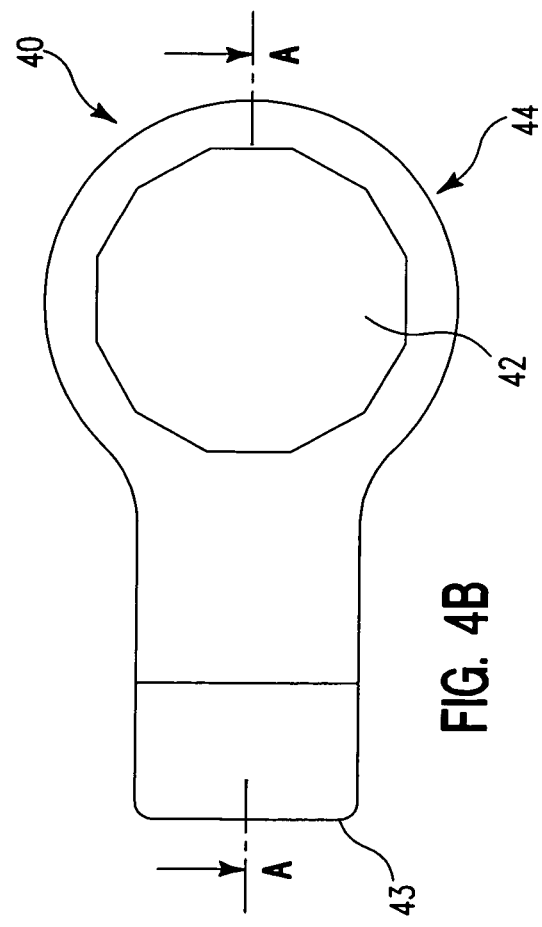
FIG. 4(B) illustrates a top view of the connector of FIG. 4(A) according to an embodiment of the invention.

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

As mentioned, there remains a need for a new and improved pedicle screw assembly capable of overcoming the limitations of the conventional designs thereby providing the surgeon with improved intra-operative flexibility and the patient with an improved prognosis for better and complete rehabilitation. The embodiments of the invention address this need by providing an improved medialised polyaxial pedicle screw device and method of assembly capable of providing greater freedom in screw placement while maintaining an adequate profile in the spinal anatomy. Referring now to the drawings and more particularly to FIGS. 1 through 10 where similar reference characters denote corresponding features consistently throughout the figures, there are shown preferred embodiments of the invention.

FIG. 1 illustrates the components of the pedicle screw assembly 10 according to an embodiment of the invention. The assembly 10 shown in FIG. 1 is for a 1-level spinal fixation construct. The bone screw (fixator component) 20, which may be embodied as a screw or hook, is pre-assembled at the factory by snapping the poly stem 30 into the bone screw 20. Alternatively, the poly stem 30 can be assembled at the time of use (i.e., during surgery). The assembly of the poly stem 30 into the bone screw 20 allows the poly stem 30 to rotate freely about the center of rotation. The bone screw 20 and poly stem 30 assembly is then inserted and "buried" into the spinal anatomy (not shown) as far as the level of the female dimples 24 (shown in FIG. 2(A)) on the bone screw 20. Once all of the needed assembled bone screws 20 are inserted into the spinal anatomy, then the respective connectors 40, ball rings 60, and longitudinal members 70 are dropped onto the poly stems 30, and the blocker pins 50 are used to lock the assembly 10 together. The longitudinal member 70 may be embodied as a rod, plate, bar, etc.

Figures 7A, 7B:
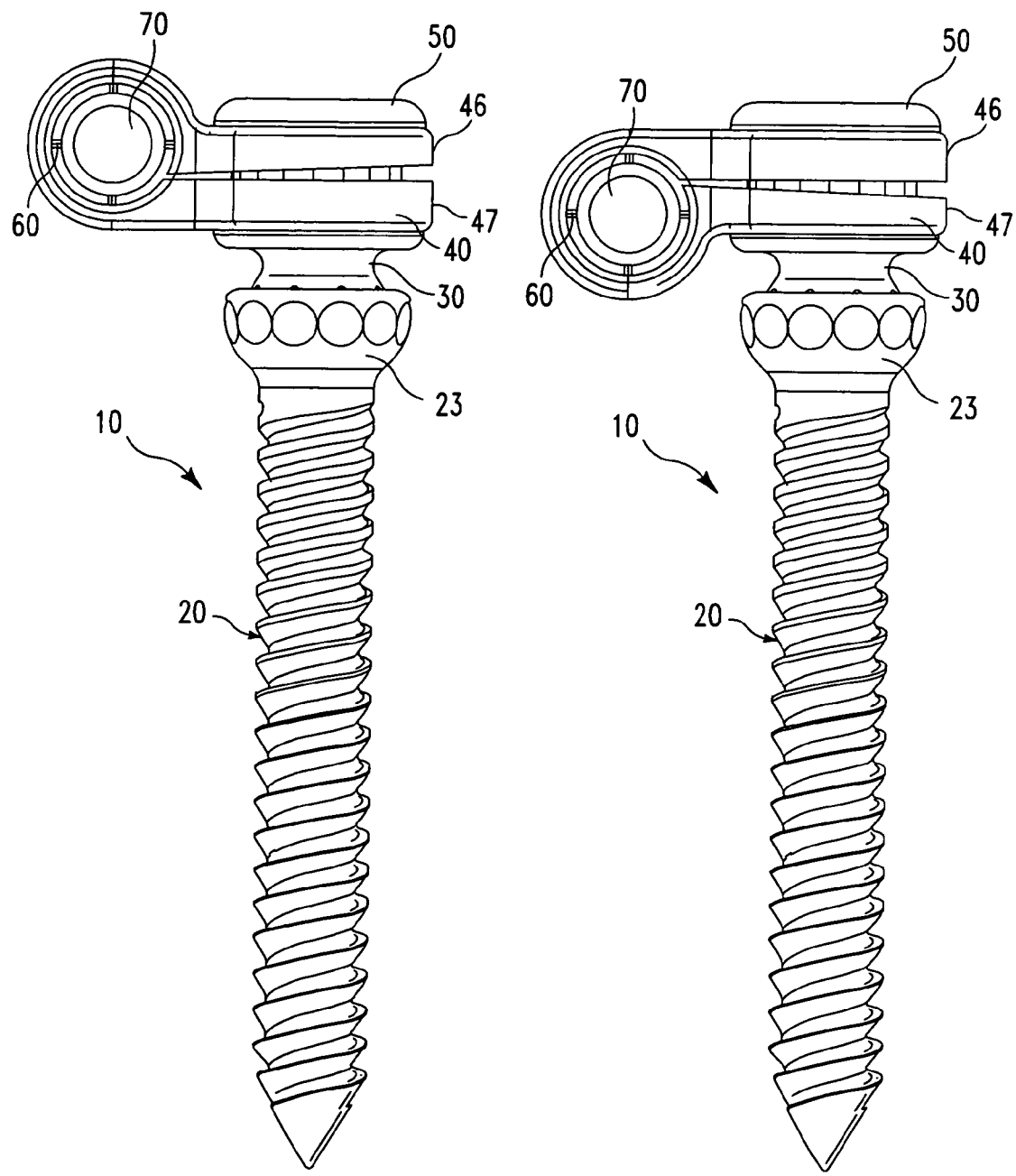
FIG. 7(A) illustrates a front view of a fully engaged screw assembly with an upright connector configuration according to an embodiment of the invention.
FIG. 7(B) illustrates a front view of a fully engaged screw assembly with an upside down connector configuration according to an embodiment of the invention.

As shown in FIGS. 2(A) through 2(D), the bone screw 20 has a threaded end 22 opposite a pocket end 23. The pocket end 23 includes a female spherical inner portion 21 with an undercut 25 to allow the poly stem 30 to pivot freely but not to disassemble once the expanding pin (blocker pin) 50 is inserted, as shown in FIGS. 7(A) through 7(B), and further described below. Again, with reference to FIGS. 2(A) through 2(D), the bone screw thread 22 may be a multiple lead thread to allow faster insertion into the bone (not shown). This thread 22 may be tapered on the minor diameter while cylindrical on the major diameter to allow a new "bite" with every turn. This also provides more thread depth towards the bottom 26 of the screw 20 for a cancellous bone (not shown).

FIGS. 3(A) through 3(D) illustrate the poly stem 30. The bottom portion of the poly stem 30 comprises a male spherical ball 31 that is slotted 35 for assembly purposes and for expansion in the final locking of the construct. The surface of the male spherical ball 31 can be treated with a rough media to create a rough texture to encourage galling with the large female spherical pocket 21 in the bone screw 20. There can be a tapered hole 36 inside the male spherical section of the poly stem 30 to encourage expansion by the blocker pin 50 as it is driven into its final locking position as shown in FIGS. 9(A) through 9(E). Again, with reference to FIGS. 3(A) through 3(D), at the top portion 33 of the poly stem 30, a plurality of flats surfaces 33 are shown to limit the torque transmission. These "flats" could alternatively be replaced by a cylindrical round surface. A lip 32 separates the top flats portion 33 with the lower ball portion 31 of the poly stem 30. Additionally, the inner surface 34 of the top portion 33 is configured with threads.

The connector 40 is shown in FIGS. 4(A) through 4(D). The geometry of the connector 40 is amenable for assembly with the spherical surface 44 either face up or down to provide multiple positions of height adjustment. The medial portion 43 of the connector 40 may be configured with a slotted section (or through hole) 41 or other various geometries to provide attachment to the longitudinal member 70 (of FIG. 1) or plate (not shown). The spherical surface 44 generally includes two prongs 46, 47 with a gap 45 configured therebetween. As such, the connector 40 is configured to be non-rigid (i.e., flexible) as it relates to the positions of the prongs 46, 47 with respect to one another. The prongs 46, 47 each include a hole 42 to accommodate the blocker pin 50 of FIG. 1. As such, when the blocker pin 50 is inserted into the hole 42 of the connector 40 and is tightened to inner threads 34 of the poly stem 30, then the prongs 46, 47 of the connector generally come together (i.e., the gap 45 is closed). The prongs 46, 47 may be configured so as to be perfectly aligned with one another or, alternatively, the prongs 46, 47 may be configured so as to stager each of the holes 42 vertically. Also the horizontal distance as provided by the gap 45 between the prongs 46, 47 is not necessarily fixed so as to allow the surgeon to use different size connectors 40 to accommodate a wider range of screw placements while conducting minimal rod bending.

Figure 5A:
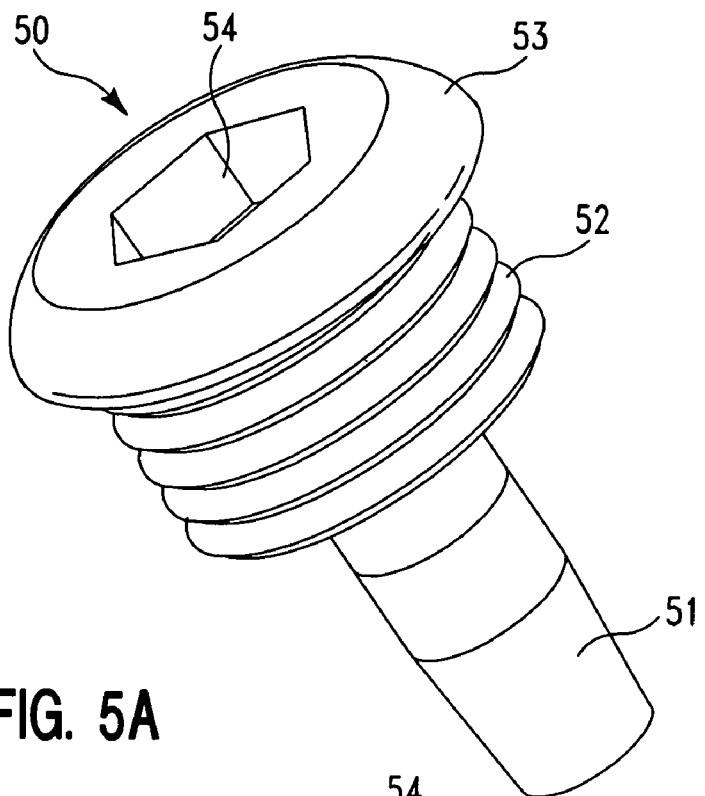
FIG. 5(A) illustrates a perspective view of the blocker pin of FIG. 1 according to an embodiment of the invention.
Figure 5B:
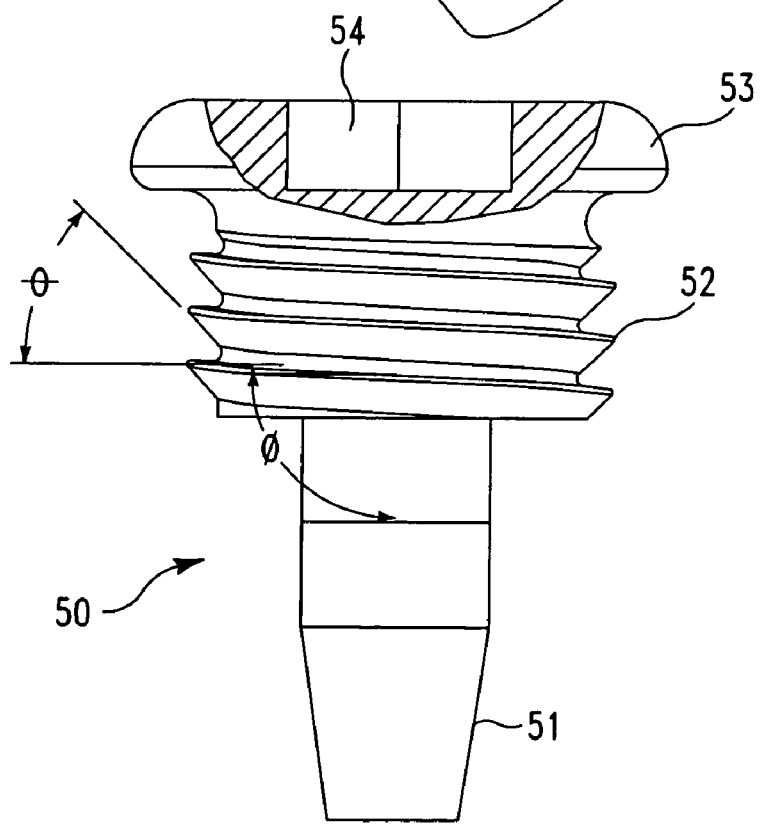
FIG. 5(B) illustrates a cross-sectional side view of the blocker pin of FIG. 5(A) according to an embodiment of the invention.

The blocker pin 50, as illustrated in FIGS. 5(A) and 5(B) (with reference to FIGS. 1 through 4(B)), includes a tapered section 51 towards the bottom, which can be used to expand and "wedge" the slotted male spherical section 31 of the poly stem 30 into the bone screw 20. The bottom of the blocker pin 50 can be rounded, flat, or pointed to "dig" in the bone screw 20 providing another method of locking the construct other than the wedging effect described above. The blocker pin 50 is also used to push down on the connector 40 to lock the longitudinal member 70 with the ball ring 60. The threads 52 on the blocker pin 50 are standard flat buttress threads. Preferably, as shown in FIG. 5(B), the thread angle, θ, equals 45° and φ equals 90°. The flat type "A" buttress thread helps prevent the poly stem 30 from loosening from the connector 40 during final tightening. On top 53 of the blocker pin 50 is an appropriate size hex aperture 54 for torque application. Furthermore, the blocker pin 50 may be configured as either a one-piece or two-piece construct, wherein the two-piece construct comprises the upper portion 53 and threaded portion 52 as one piece and the tapered lower section 51 as the second piece, wherein the two separate pieces are configured such that they are free to rotate relative to one another so as to not encourage galling during final locking of the assembly 10.

Figure 8B:
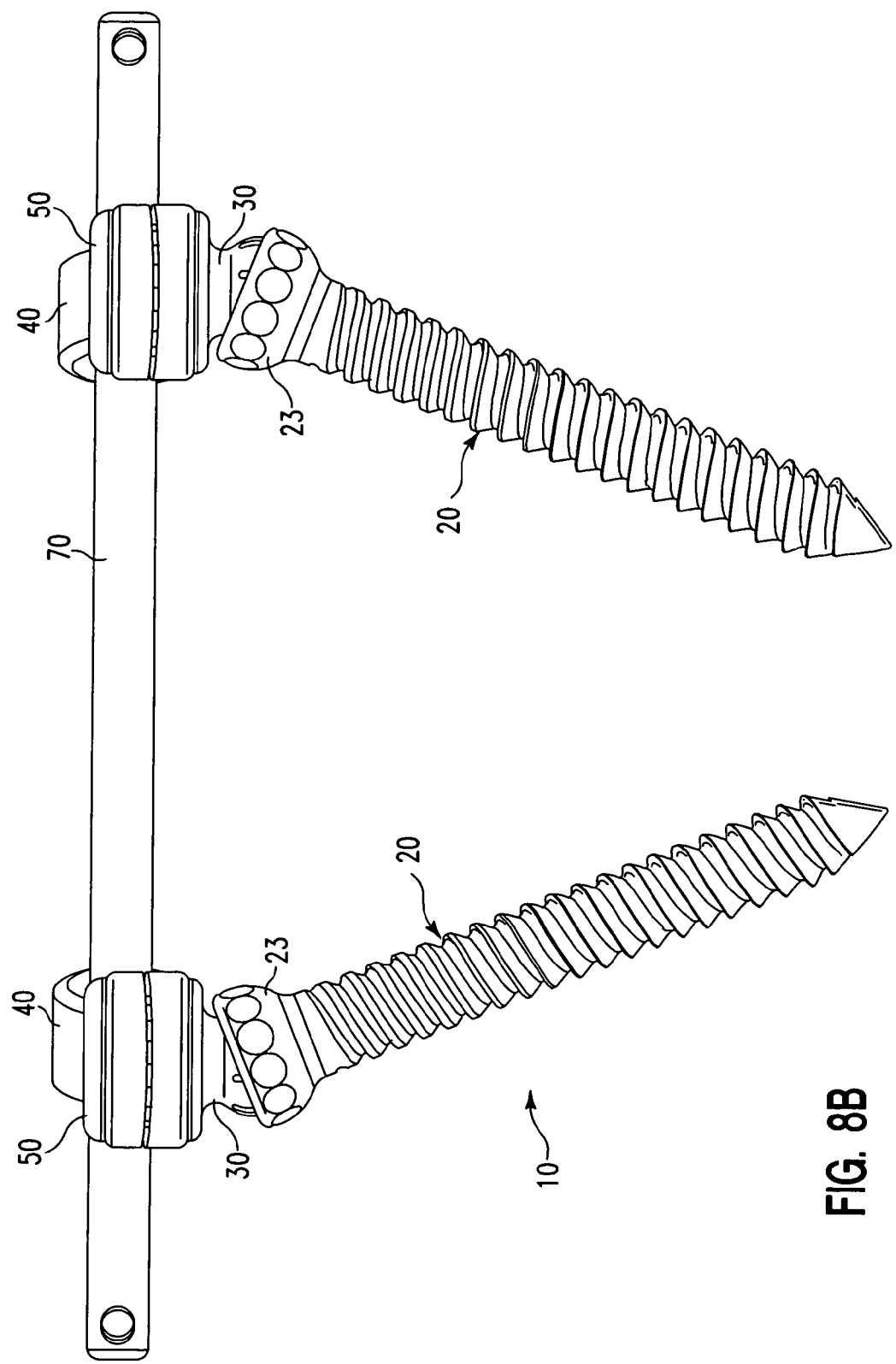
FIG. 8(B) illustrates a front view of a fully engaged screw assembly in various stages of angulation with an upside down connector configuration according to an embodiment of the invention.

FIGS. 6(A) through 6(C) show the ball ring 60. The ball ring 60 has a generally spherical or cylindrical body 62 and trans-radial cuts 61 defined in the body 62. The spherical body portion 62 of the ball ring 60 allows the angulation of the longitudinal member position. The various angulation scenarios are shown in FIGS. 7(A) through 8(B). The medial angulation of the socket 23 of the bone screw 20 is equal in the alternative assembly configuration of FIGS. 7(A) and 7(B). In FIG. 7(A), the connector 40 is positioned in its normal configuration, while in FIG. 7(B), the connector 40 is positioned upside down. The angulations shown in FIGS. 8(A) and 8(B) show a height difference depending on the assembly configuration. For example, if a connector 40 is assembled as shown in FIG. 8(B), the height and the angulation of the bone screw 20 is dependant on the angles created by the poly stem 30, the ball ring 60, and the choice of the assembly method of the connector 40 (normal configuration (FIG. 8(A) versus upside down configuration (FIG. 8(B)).

Figure 9A:
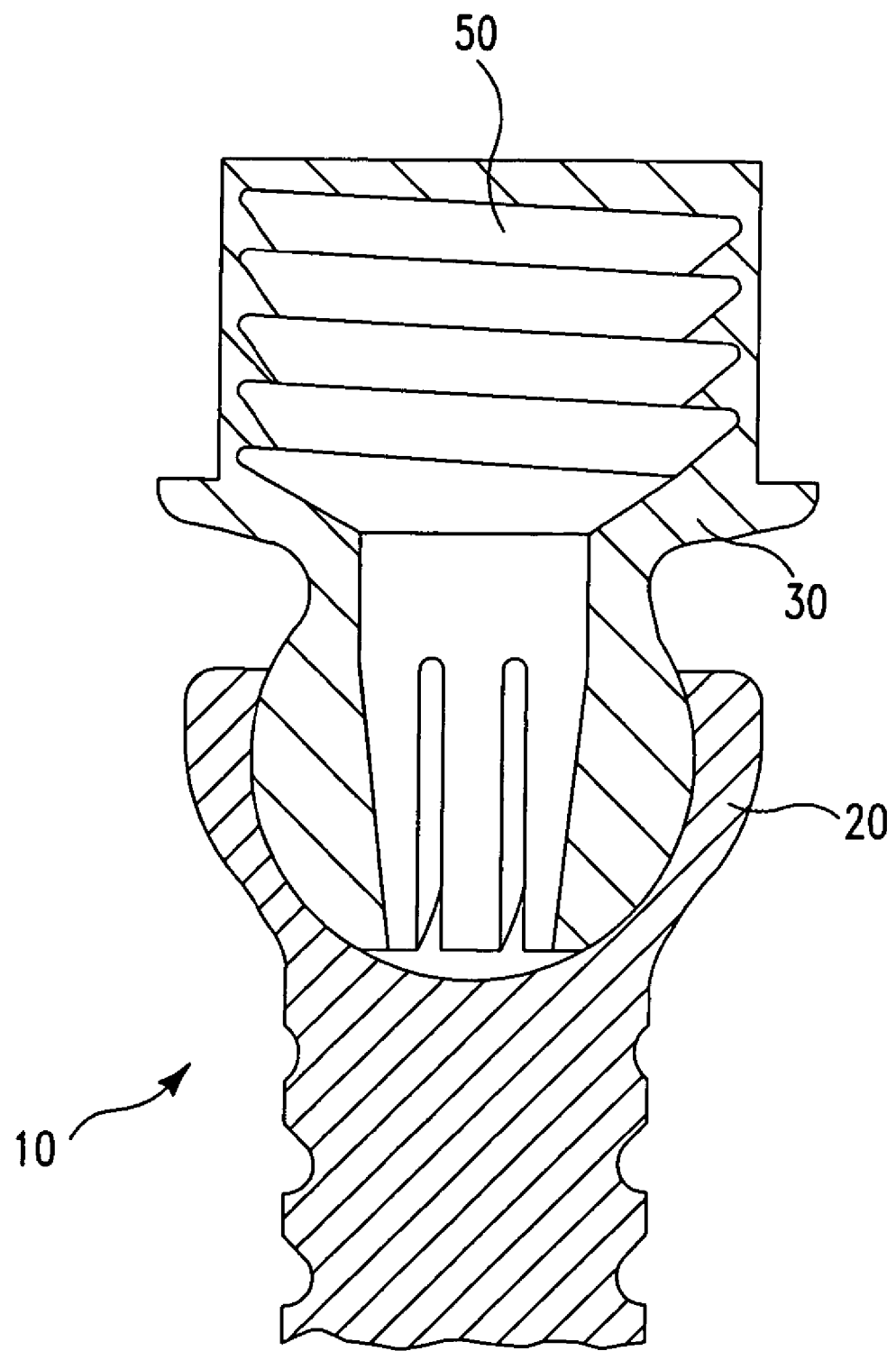
FIGS. 9(A) through 9(E) illustrate several views of a screw assembly in various stages of assembly and engagement according to an embodiment of the invention.

In terms of manufacturing the assembly 10, FIGS. 9(A) through 9(E) illustrate various sectional views of the assembly 10. As shown in FIG. 9(A), if a user wants to assemble the poly stem 30 at the time of usage (i.e., during surgery), the poly stem 30 could be omitted at the factory assembly stage of manufacturing. At the factory assembly stage of manufacturing, the poly stem 30 can rotate freely inside the bone screw 20. The connector 40, ball ring 60, and longitudinal member 70 (not shown in FIG. 9(A)) are then dropped into the poly stem 30. At this point, the angle of the poly stem 30 could be adjusted to the desired position. The blocker pin 50 is inserted into the connector 40, and then into the poly stem 30, thereby preventing the longitudinal member 70 from escaping once the blocker pin 50 is engaged. The blocker pin 50 is now ready to apply downward forces on the connector 40, ball ring 60, and longitudinal member 70 sub-assembly. Also, the blocker pin 50 transmits forces to the poly stem 30 and the bone screw 20.

Figure 9B:
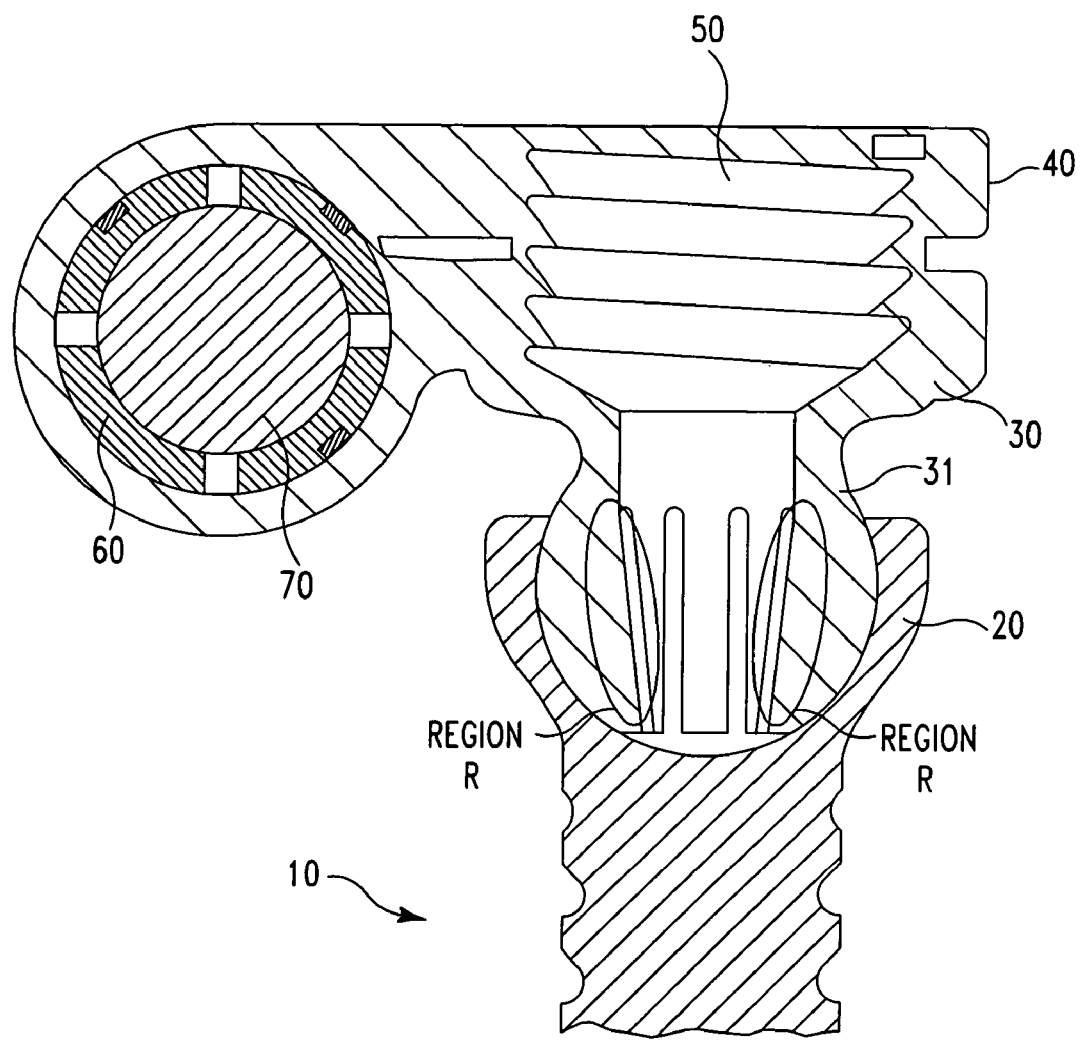

The blocker pin 50 is fully tightened to a predetermined torque. The blocker pin 50 is driven into the bone screw 20 while expanding the poly stem 30. The bulbous end 31 of the poly stem 30 has very little room to expand. The wedging effect locks the construct 10 at the desired orientation. FIG. 9(E) illustrates a sectional-view of the construct 10 in the locked position. As shown, the blocker pin 50 has penetrated the bone screw 20 and "lifted" the male spherical portion 31 of the poly stem 30 wedging the poly stem 30 further into the bone screw 20.

Generally, the assembly 10 locks because of the engagement between the bone screw 20 and the poly stem 30 from the force transmitted by the blocker pin 50. The engaging system generally includes three stages: (1) before engaging (FIG. 9(B)); (2) start to engage (FIG. 9(C)); (3) fully engaged (FIGS. 9(D) and 9(E)). The performance of each component (bone screw 20, poly stem 30, and blocker pin 50) varies per stage. As shown in FIG. 9(B) (before engaging), the blocker pin 50 has yet to transmit forces to the poly stem 30 or to the bone screw 20. The blocker pin 50 sits in region R (denoted by the elliptical circles). In this stage, the blocker pin 50 has no freedom to move. However, the poly stem 30 still has a freedom of rotation.

Figure 9C:
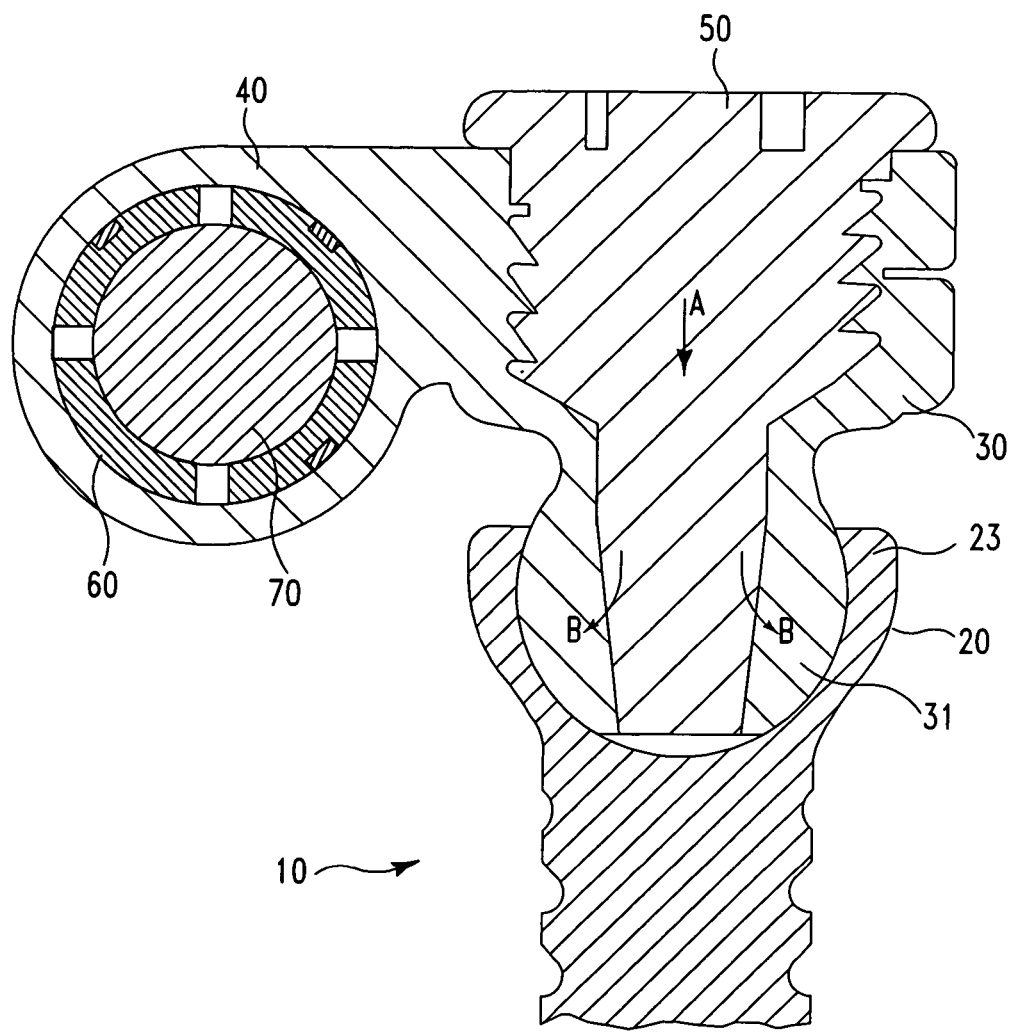
Figure 9D:
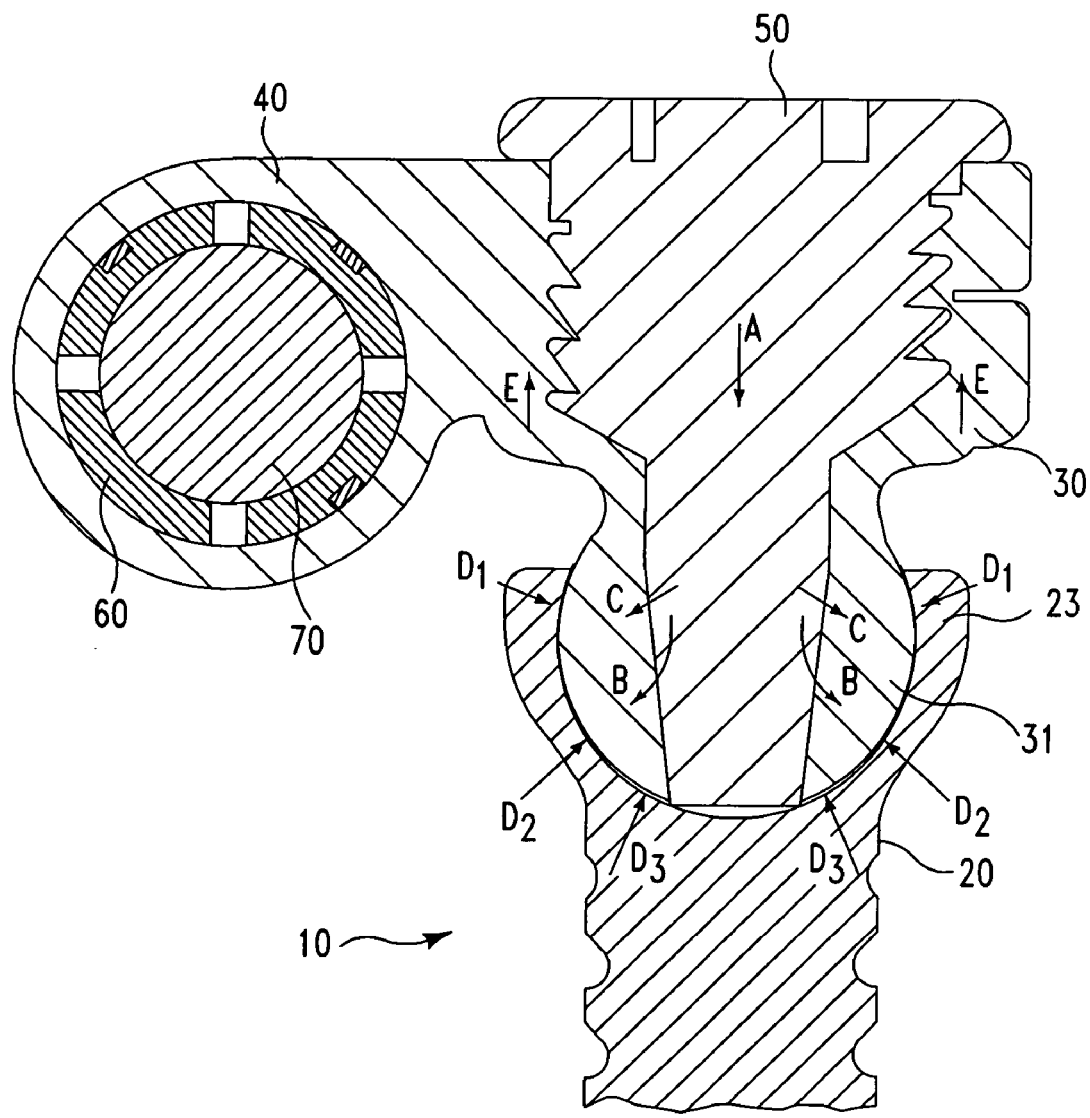
Figure 9E:
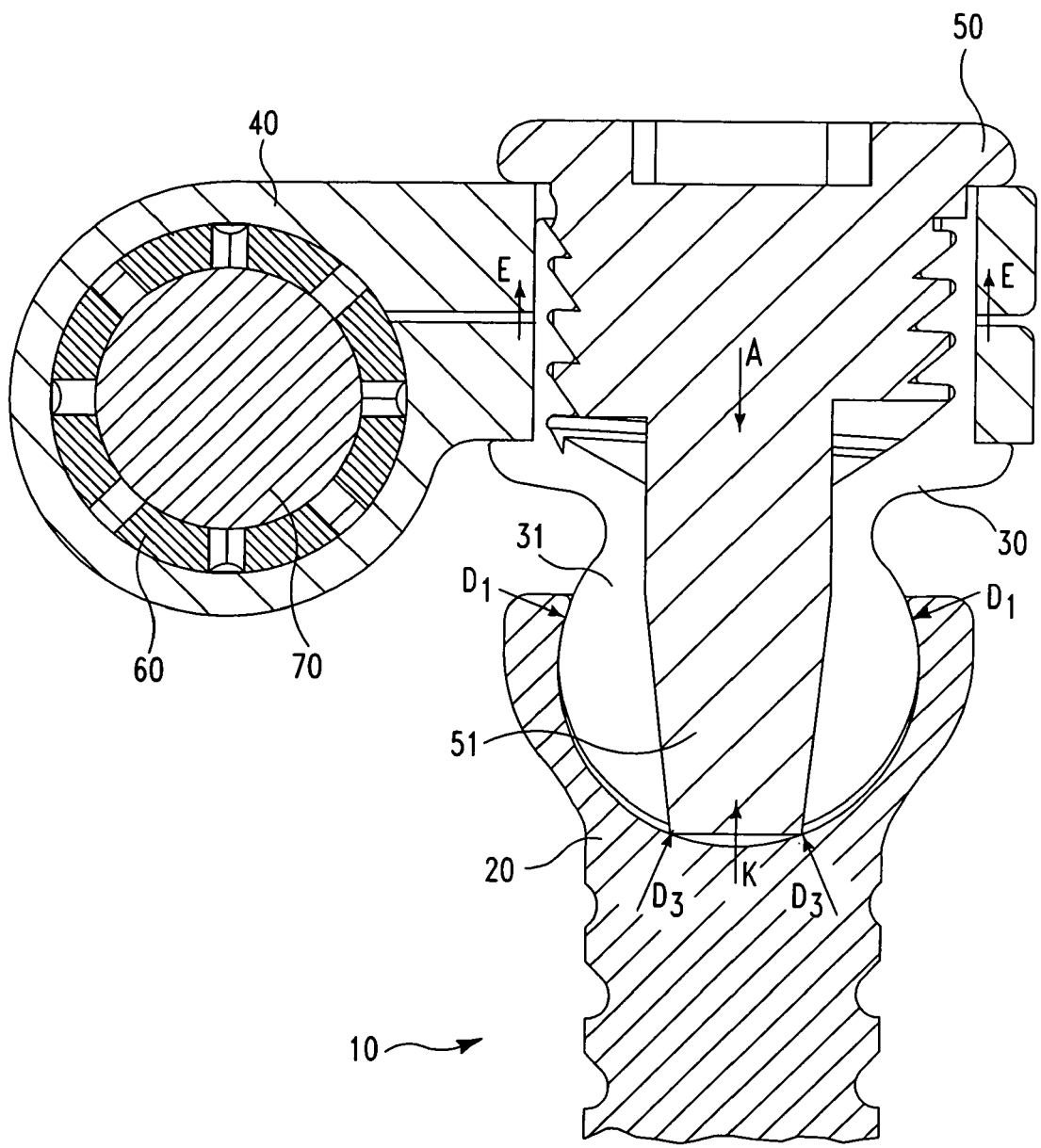

As shown in FIG. 9(C), the blocker pin 50 starts to engage. Force A is transmitted by the blocker pin 50 forcing the area of contact to increase accordingly. Enough contact force is generated to bend (denoted by force B) the male sphere 31 of the poly stem 30. At this stage, the blocker pin 50 begins to contact the female sphere 23 of the bone screw 20. As shown in FIG. 9(D), the blocker pin 50 is fully engaged. The blocker pin 50 pushes downward against the connector 40 and the poly stem 30 and creates a force A. Force A is then separated into three forces: C, B, and $D_3$. Forces $D_3$ are pushing against the female sphere 23 of the bone screw 20 thereby creating force E and driving the poly stem 30 upward. By the poly stem 30 moving upward, force $D_1$ is created. Finally, the locking mechanism is completed when forces $D_1$, $D_2$, and $D_3$ create a wedge between the poly stem 30 and the bone screw 20 by working against forces C and E.

Since the major engaging component is executed by the forces $D_1$ and $D_3$, the above-described engaging method could be substituted by the following: bending forces B and the expansion forces C are ignored or removed. The forces $D_2$ are removed since the forces B and C are ignored or removed. Then, the contact forces $D_3$ are increased at the bulbous end 31 of the poly stem 30 and the forces $D_1$ acting on the opening of the bone screw 20. As such, FIG. 9(E) illustrates an alternative possibility of engaging the assembly 10. In this case, the force A is transmitting to the bone screw 20 and thereby creating the reaction forces $D_3$ or K, and depends on the shape of the tapered end 51 of the blocker pin 50. Again, forces $D_3$ or K are pushing against the female sphere of the bone screw 20, creating force E, and driving the poly stem 30 upward. By the poly stem 30 moving upward, force $D_1$ is created. Finally, the locking mechanism is completed when forces $D_1$ and $D_3$ (or K) created a wedge between the poly stem 30 and the bone screw 20 by working against forces E.

Figure 10:
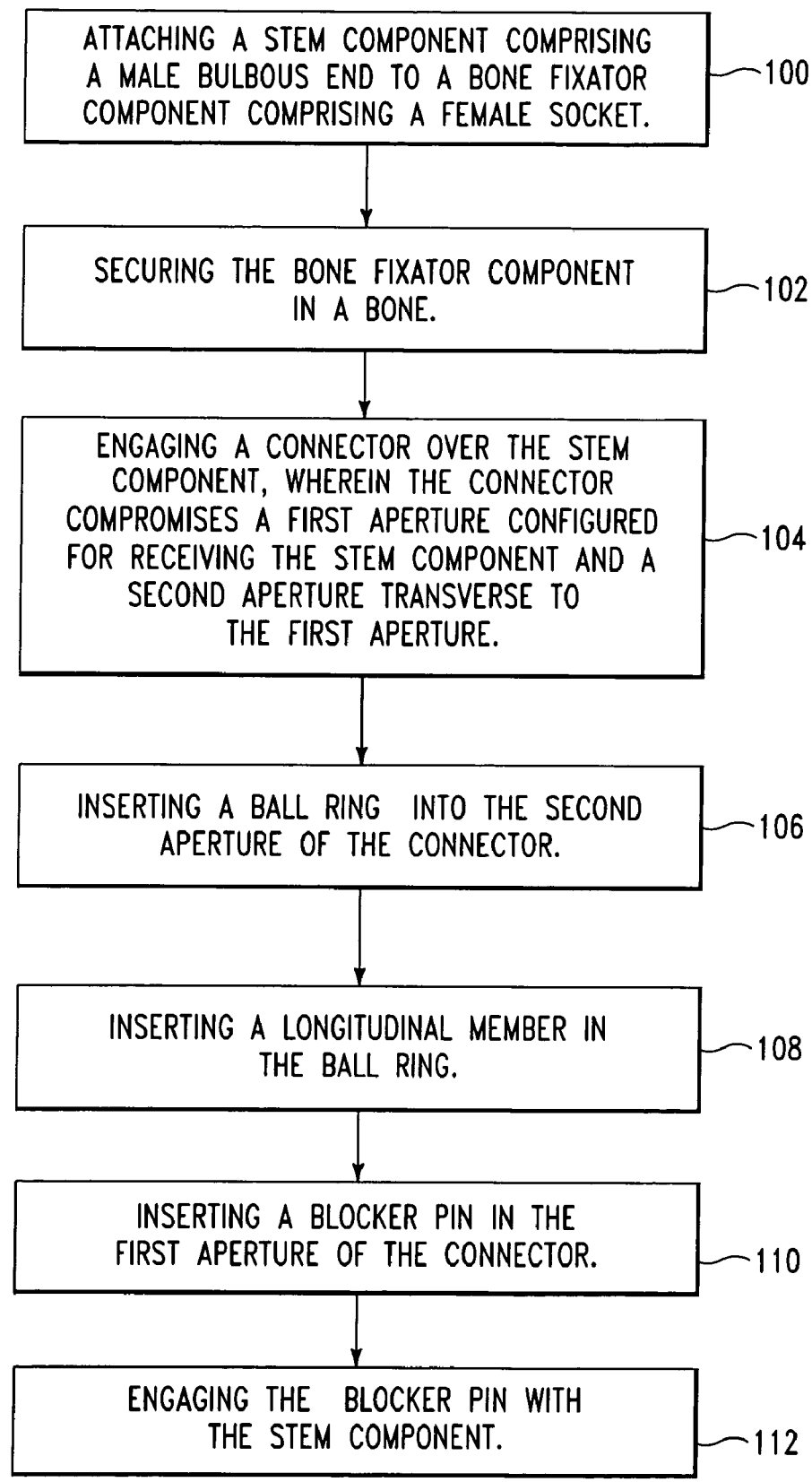
FIG. 10 is a flow diagram illustrating a preferred method according to an embodiment of the invention.

FIG. 10 (with reference to the components provided in FIGS. 1 through 9(E)) is a flow diagram illustrating a method of assembling a pedicle screw assembly 10, wherein the method comprises attaching (100) a stem component 30 comprising a male bulbous end 31 to a bone fixator component 20 comprising a female socket 21; securing (102) the bone fixator component 20 in a bone (not shown); engaging (104) a connector 40 over the stem component 30, wherein the connector 40 comprises a first aperture 42 configured for receiving the stem component 30 and a second aperture 41 transverse to the first aperture 42; inserting (106) a ball ring 60 into the second aperture 41 of the connector 40; inserting (108) a longitudinal member 70 in the ball ring 60; inserting (110) a blocker pin 50 in the first aperture 42 of the connector 40; and engaging (112) the blocker pin 50 with the stem component 30. Moreover, the engagement of the blocker pin 50 with the stem component 30 causes expansion of the male bulbous end 31 of the stem component 30 in the female socket 21 of the bone fixator component 20. Additionally, the engagement of the blocker pin 50 with the stem component 30 causes tightening of the ball ring 60 thereby causing the ball ring 60 to secure the longitudinal member 70.

The embodiments of the invention provide a polyaxial spinal screw assembly 10 that provides greater freedom in screw placement while maintaining an adequate profile in the spinal anatomy. The added freedom is accomplished by having three separate features that offer various degrees of flexibility. The embodiments of the invention also provide greater freedom by allowing the surgeon to place the connector 40 upside down or right side up to accommodate various heights on the longitudinal member 70 without leaving the anchor part outside the anchor anatomy. The assembly 10 provides a lower profile by allowing the polyaxial center of rotation to be buried within the pedicle or anatomy thereby gaining valuable space to fasten the longitudinal member 70 or plate (not shown). In an alternative embodiment, a ceramic coated ball joint is used for improved wear resistance that would not be rigid, but rather, would offer a predetermined resistance force to function as a dynamic rod system to provide load sharing with the natural human disc or an artificial disk.

Generally, as illustrated in FIGS. 1 through 6(B), the embodiments of the invention provide an assembly 10 comprising a ball ring 60; a stem component 30 comprising a bulbous end 31; a fixator component 20 adapted to receive the bulbous end 31 of the stem component 30; and a connector 40 comprising a first aperture 42; and a second aperture 41. The assembly 10 further comprises a blocker pin 50 adapted to engage the stem component 30. Preferably, the fixator component 20 comprises a threaded end 22; and a pocket end 23 opposite the threaded end 22, wherein the pocket end 23 preferably comprises a concave inner portion 21 and a dimpled outer portion 24. The stem component 30 preferably further comprises a threaded open end 34 opposite the bulbous end 31, wherein the bulbous end 31 comprises a plurality of slots 35. The stem component 30 also includes a hole 36 in the bulbous end 31 and terminating at the plurality of slots 35, wherein the hole 36 is adapted to receive the blocker pin 50.

The ball ring 60 preferably comprises a curved body 62 having a plurality of trans-radial cuts 61; and a hole 63 configured in the curved body 62 and adapted to receive a longitudinal member 70. The first aperture 42 of the connector 40 is adapted to receive the stem component 30. The second aperture 41 of the connector 40 is adapted to accommodate the ball ring 60 and to receive the longitudinal member 70, wherein the second aperture 41 is transverse to the first aperture 42.

The connector 40 preferably comprises a medial portion 43 comprising the second aperture 41; and a pair of prongs 46, 47 connected by the medial portion 43, wherein the pair of prongs 46, 47 comprise the first aperture 42, and wherein the connector 40 may comprise a gap 45 separating the pair of prongs 46, 47 from one another. The blocker pin 50 comprises a lower section 51 adapted to fit into the hole 36 in the bulbous end 31 of the stem component 30; a threaded portion 52 adjacent to the lower section 51 and adapted to mate with the threaded open end 34 of the stem component 30; and an upper section 53 adjacent to the threaded portion 52, wherein the upper section 53 is adapted to engage one of the pair of prongs 46 or 47 of the stem component 30. Preferably, each of the bulbous end 31 of the stem component 30 and the ball ring 60 are bendable.

The embodiments of the invention provide an improvement in the field of surgical lumbar and thoracic and cervical spine treatment. Moreover, the embodiments of the invention may be used anteriorly or posteriorly. The embodiments of the invention can be utilized in surgeries to achieve anterior lumbar interbody fusion, posterior lumbar interbody fusion, transverse lumbar interbody fusion, degenerative disc disease, adult and pediatric scoliosis as a fixation device, and posterior cervical fusion.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments of the invention have been described in terms of preferred embodiments, those skilled in the art will recognize that the embodiments of the invention can be practiced with modification within the spirit and scope of the appended claims.

What is claimed is:

1. An assembly comprising:
   a bendable ball ring;
   a stem component comprising a bendable and expandable round hollow male bulbous end;
   a bone fixator component comprising a female socket that receives said bulbous end of said stem component;
   a connector comprising:
     a first aperture that receives said stem component; and
     a second aperture that receives said bendable ball ring, wherein said second aperture is positioned transverse to said first aperture;
   a blocker pin that engages said stem component and expands said bulbous end; wherein said stem component further comprises: a threaded open end opposite said bulbous end, wherein said bulbous end comprises a plurality of slots; and a hole in said bulbous end terminating at said plurality of slots, wherein said hole receives said blocker pin.

2. The assembly of claim 1, wherein said bone fixator component comprises:
   a threaded end; and
   a pocket end opposite said threaded end.

3. The assembly of claim 2, wherein said pocket end comprises:
   a concave inner portion; and
   a dimpled outer portion.

4. The assembly of claim 1, wherein said ball ring comprises:
   a curved body having a plurality of trans-radial cuts; and
   a hole configured in said curved body and adapted to receive a longitudinal member.

5. The assembly of claim 4, wherein said second aperture accommodates said ball ring and receives a longitudinal member.

6. The assembly of claim 1, wherein said first aperture receives an open end of said stem component, and wherein said open end of said stem component is positioned opposite to said bulbous end.

7. The assembly of claim 1, wherein said connector comprises:
   a medial portion comprising said second aperture; and
   a pair of prongs connected by said medial portion, wherein said pair of prongs comprise said first aperture.

8. The assembly of claim 7, further comprising a gap separating said pair of prongs.

9. The assembly of claim 7, wherein said blocker pin comprises:
   a lower section that fits into said hole in said bulbous end of said stem component;
   a threaded portion adjacent to said lower section and adapted to mate with said threaded open end of said stem component; and
   an upper section adjacent to said threaded portion.

10. The assembly of claim 9, wherein said upper section engages one of said pair of prongs of said stem component.

11. The assembly of claim 1, wherein said bulbous end locks into said female socket.

12. A pedicle screw assembly comprising:
    a longitudinal member;
    a bendable ball ring adapted to receive said longitudinal member;
    a poly stem comprising a bendable male bulbous end;
    a connector comprising:
      a pair of first apertures adapted to receive said poly stem;
      a second aperture adapted to receive said ball ring and said longitudinal member, wherein said second aperture is transverse to said first aperture;
      a medial portion comprising said second aperture; and
      a pair of prongs connected by said medial portion, wherein said pair of prongs comprise said pair of first apertures;
    a bone fixator component comprising a female socket adapted to receive said poly stem; and
    a blocker pin adapted to engage said poly stem and to secure said longitudinal member.

13. The assembly of claim 12, wherein said poly stem further comprises:

a threaded open end opposite said bulbous end, wherein said bulbous end comprises a plurality of slots;

a hole in said bulbous end terminating at said plurality of slots, wherein said hole is adapted to receive said blocker pin.

14. The assembly of claim 13, wherein said blocker pin comprises:

a lower section adapted to fit into said hole in said bulbous end of said poly stem;

a threaded portion adjacent to said lower section and adapted to mate with said threaded open end of said poly stem; and an upper section adjacent to said threaded portion, wherein said upper section is adapted to engage one of said pair of prongs of said poly stem.

15. The assembly of claim 12, wherein said pair of first apertures is adapted to receive said poly stem.

16. The assembly of claim 12, wherein said bulbous end fits into said female socket.

17. A method of assembling a pedicle screw assembly, said method comprising:

attaching a stem component comprising a male bulbous end to a bone fixator component comprising a female socket;

securing said bone fixator component in a bone;

engaging a connector over said stem component, wherein said connector comprises:

a first aperture for receiving said stem component;

a second aperture transverse to said first aperture;

a medial portion comprising said second aperture; and a pair of prongs connected by said medial portion, wherein said pair of prongs comprise said first aperture;

inserting a ball ring into said second aperture of said connector;

inserting a longitudinal member in said ball ring;

inserting a blocker pin in said first aperture of said connector; and engaging said blocker pin with said stem component.

18. The method of claim 17, wherein engagement of said blocker pin with said stem component causes expansion of said male bulbous end of said stem component in said female socket of said bone fixator component.

19. The method of claim 17, wherein engagement of said blocker pin with said stem component causes tightening of said ball ring thereby causing said ball ring to secure said longitudinal member.

* * * * *